(12) United States Patent
Adams et al.

(10) Patent No.: US 11,484,377 B2
(45) Date of Patent: Nov. 1, 2022

(54) RAIL TENSION EXTRACTION DEVICES

(71) Applicant: Grey Matter Medical Products, Ridgefield, WA (US)

(72) Inventors: Kevin Adams, Portland, OR (US); Cory Dobak, Ridgefield, WA (US); Kevin Pyatt, Culver, OR (US)

(73) Assignee: Grey Matter Medical Products, Vancouver, WA (US)

( * ) Notice: Subject to any disclaimer, the term of this patent is extended or adjusted under 35 U.S.C. 154(b) by 362 days.

(21) Appl. No.: 16/672,215

(22) Filed: Nov. 1, 2019

(65) Prior Publication Data

US 2020/0138535 A1 May 7, 2020

Related U.S. Application Data

(60) Provisional application No. 62/754,719, filed on Nov. 2, 2018.

(51) Int. Cl.
*A61B 17/00* (2006.01)
*A61B 34/00* (2016.01)

(52) U.S. Cl.
CPC .... *A61B 34/73* (2016.02); *A61B 2017/00336* (2013.01); *A61B 2017/00349* (2013.01);
(Continued)

(58) Field of Classification Search
CPC ...... A61B 2034/731; A61B 2017/2217; A61B 2017/2212; A61B 2017/22035;
(Continued)

(56) References Cited

U.S. PATENT DOCUMENTS

| 3,835,864 A | 9/1974 | Rasor et al. |
| RE30,366 E | 8/1980 | Rasor et al. |

(Continued)

FOREIGN PATENT DOCUMENTS

CN 201410193340 A 11/2015

OTHER PUBLICATIONS

International Search Report and Written Opinion prepared by the US Patent and Trademark Office for PCT/US2019/059518, dated Mar. 25, 2020, 13 pages.
(Continued)

*Primary Examiner* — Jocelin C Tanner
(74) *Attorney, Agent, or Firm* — Chernoff, Vilhauer, McClung & Stenzel, LLP (57) ABSTRACT

Rail tension extraction devices and methods of extracting target(s) inside a patient's body are disclosed. The device includes a base assembly having a handle and an elongate base. The device additionally includes at least one magnet configured to engage a metallic target, and a capture element received in the base assembly and disposed adjacent to the at least one magnet. The capture element is configured to at least partially surround the metallic target engaged by the at least one magnet. The device further includes an outer tube configured to move relative to the elongate base between a locking position in which a distal end of the outer tube is adjacent the capture element and the at least one magnet to secure the metallic target therebetween, and an unlocking position in which the distal end of the outer tube is spaced from the capture element and the at least one magnet.

17 Claims, 9 Drawing Sheets

(52) U.S. Cl.
CPC ............... *A61B 2017/00367* (2013.01); *A61B 2017/00876* (2013.01); *A61B 2034/731* (2016.02)

(58) Field of Classification Search
CPC .. A61B 2017/00876; A61B 2017/0078; A61B 2017/00367; A61B 2017/00349; A61B 2017/00336; A61B 2017/2944; A61B 2017/2945; A61B 2017/2904; A61B 2017/2926; A61B 34/73; A61B 17/221; A61B 17/22031
See application file for complete search history.

(56) References Cited

U.S. PATENT DOCUMENTS

| | | | |
|---|---|---|---|
| 4,790,809 A | 12/1988 | Kuntz | |
| 4,865,030 A | 9/1989 | Polyak | |
| 4,988,347 A | 1/1991 | Goode et al. | |
| 5,364,404 A | 11/1994 | Jaffe et al. | |
| 5,928,261 A | 7/1999 | Ruiz | |
| 6,551,304 B1 | 4/2003 | Whalen et al. | |
| 6,554,842 B2 | 4/2003 | Heuser et al. | |
| 7,390,324 B2 | 6/2008 | Whalen et al. | |
| 7,618,435 B2 | 11/2009 | Opolski | |
| 7,799,050 B2 | 9/2010 | Hensley et al. | |
| 7,873,401 B2 | 1/2011 | Shachar | |
| 8,185,176 B2 | 5/2012 | Mangat et al. | |
| 8,715,205 B2 | 5/2014 | Carter et al. | |
| 8,892,217 B2 | 11/2014 | Camps et al. | |
| 9,126,032 B2 | 9/2015 | Khairkhahan et al. | |
| 9,492,674 B2 | 11/2016 | Schmidt et al. | |
| 9,504,820 B2 | 11/2016 | Bonner et al. | |
| 9,700,732 B2 | 7/2017 | Schmidt et al. | |
| 2005/0033314 A1 | 2/2005 | Sakurai et al. | |
| 2008/0147061 A1* | 6/2008 | Goode | A61B 18/1492 606/45 |
| 2009/0046238 A1* | 2/2009 | Daishi | G02F 1/13394 349/155 |
| 2009/0157115 A1 | 6/2009 | Fleming | |
| 2011/0098720 A1 | 4/2011 | Taylor et al. | |
| 2011/0175693 A1 | 7/2011 | Chang | |
| 2011/0276075 A1 | 11/2011 | Fung et al. | |
| 2012/0109148 A1 | 5/2012 | Bonner et al. | |
| 2012/0109149 A1 | 5/2012 | Bonner et al. | |
| 2012/0155910 A1 | 6/2012 | Sato | |
| 2013/0066136 A1* | 3/2013 | Palese | A61B 34/73 600/11 |
| 2014/0364866 A1* | 12/2014 | Dryden | A61B 17/221 606/113 |
| 2016/0081691 A1 | 3/2016 | Gittard | |
| 2016/0235442 A1 | 8/2016 | Palese et al. | |
| 2017/0027582 A1* | 2/2017 | Khoury | A61B 17/221 |
| 2019/0046238 A1* | 2/2019 | Jenkins | A61B 17/221 |

OTHER PUBLICATIONS

European Search Report, 19879942.1—1113/3873359 PCT/US2019059518, dated Jun. 15, 2022, 6 pgs.

* cited by examiner

RAIL TENSION EXTRACTION DEVICES

CROSS REFERENCE TO RELATED APPLICATION

This application claims priority to U.S. Provisional Patent Application No. 62/754,719, filed Nov. 2, 2018. The complete disclosure of the above application is hereby incorporated by reference for all purposes.

BACKGROUND OF THE INVENTION

Medical devices, such as catheters, wire guides, cardiac leads and the like, have long been used to treat and improve the health of patients. Unfortunately, these devices occasionally break, fracture, or fragment during use. Once broken or fragmented, a piece of a device can be released into the vascular system or elsewhere in the patient, even from such simple procedures as intravenous infusion or intravenous pressure monitoring. Any foreign body in the bloodstream has the potential to cause several clinical complications, including sepsis, perforation, thrombosis, arrhythmia, myocardial necrosis, and on occasion, even death. When such risk is encountered, it is urgent and vital to remove the foreign body from the patient, and a variety of approaches are known for such removal.

Open surgery is effective for removing a foreign body or article from the vascular system of a patient. However, open surgery is costly, is traumatic to the patient, requires long periods of patient healing and recovery, and entails its own risks of further complications. These risks are often disproportionate to a patient who has only undergone a routine, noninvasive vascular access procedure.

Retrieval devices for removing a foreign body or article are available but suffer from limitations due to inconsistent engagement of the target from the lack of imaging capabilities to guide retrieval of that foreign body or article in a consistent and predictable manner. Such inconsistent engagement of the target results in potentially long procedure times and excess imaging. What is desired in a retrieval devices that provides consistent engagement of the target to facilitate removal of the foreign body or article.

BRIEF DESCRIPTION OF THE DRAWINGS

For a better understanding of the present disclosure, and to show how the same may be carried into effect, reference will now be made, by way of example, to the accompanying drawings, in which.

DETAILED DESCRIPTION

Referring to FIGS. 1-6, an example of a rail tension extraction device of the present disclosure is generally indicated at 20. Unless explicitly excluded, rail tension extraction device 20 may additionally, or alternatively, include one or more components of the other rail tension extraction devices of the present disclosure. Rail tension extraction device 20 includes a base assembly 22, an engagement assembly 24, a securing assembly 26, and a locking assembly 28. In the example shown in FIGS. 1-6, the rail tension extraction device also includes a fluid assembly 30, but other examples of the device may exclude that assembly.

Base assembly 22 includes any suitable structure configured to support and/or contain (and/or partially contain) one or more other components of the rail tension extraction device. In the example shown in FIGS. 1-6, the base assembly includes a handle 32 and an elongate base 34 having a first end portion 36 and an opposed second end portion 38. Handle 32 is attached to the first end portion of the elongate base. The elongate base may have any dimensions suitable for extracting targets from inside a patient based on a desired access point, such as the femoral vein, subclavian vein, innominate vein, superior vena cava (SV), inferior vena cava (IVC), etc. Although elongate base 34 has a cylindrical shape (sometimes referred to as an "elongate tube"), the base assembly may include an alternatively shaped elongate base attached to the handle, such as having the shape of a triangular-prism or a cuboid.

Figure 1:
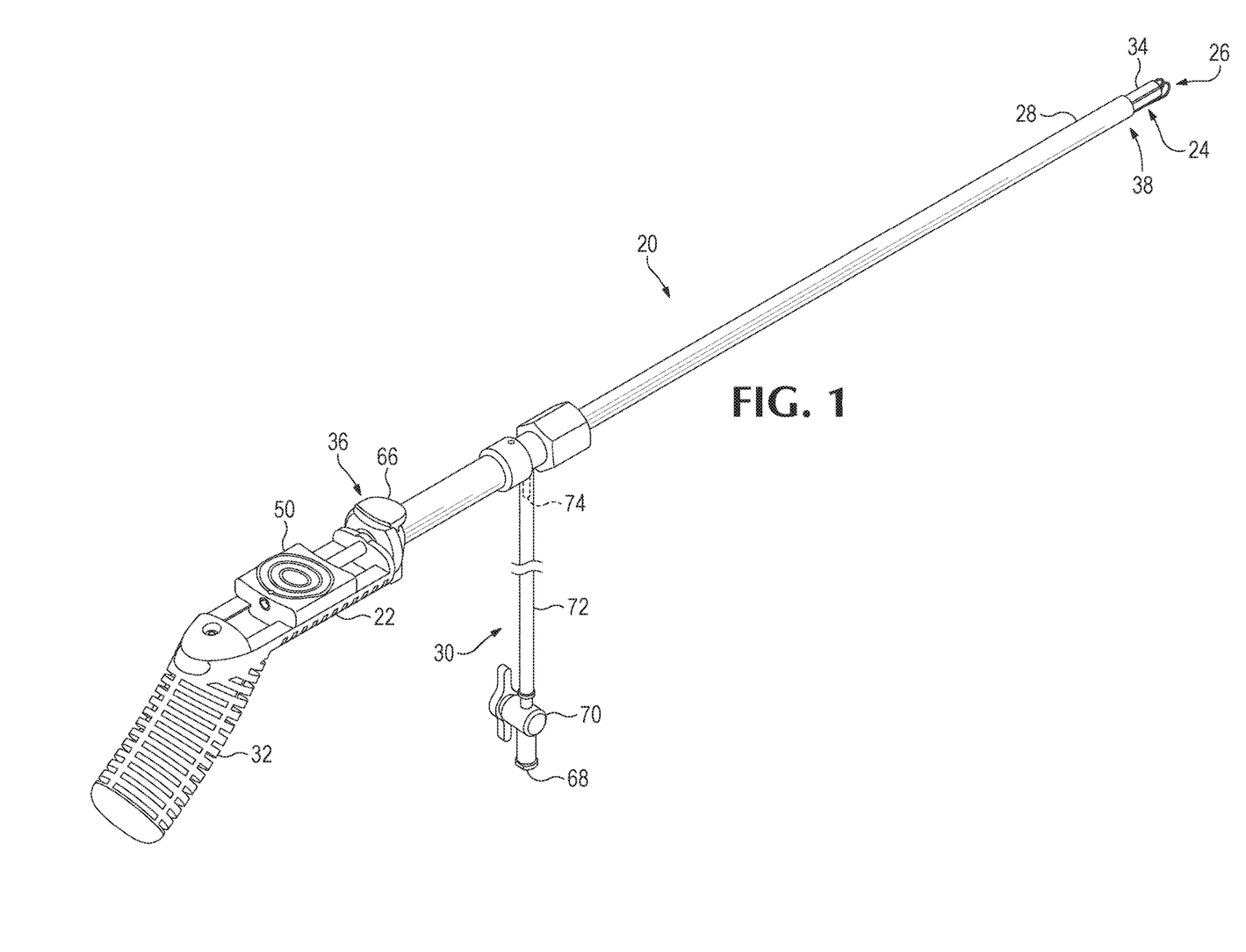
FIG. 1 is a perspective view of an example of a rail tension extraction device of the present disclosure.
Figures 2, 3, 4:
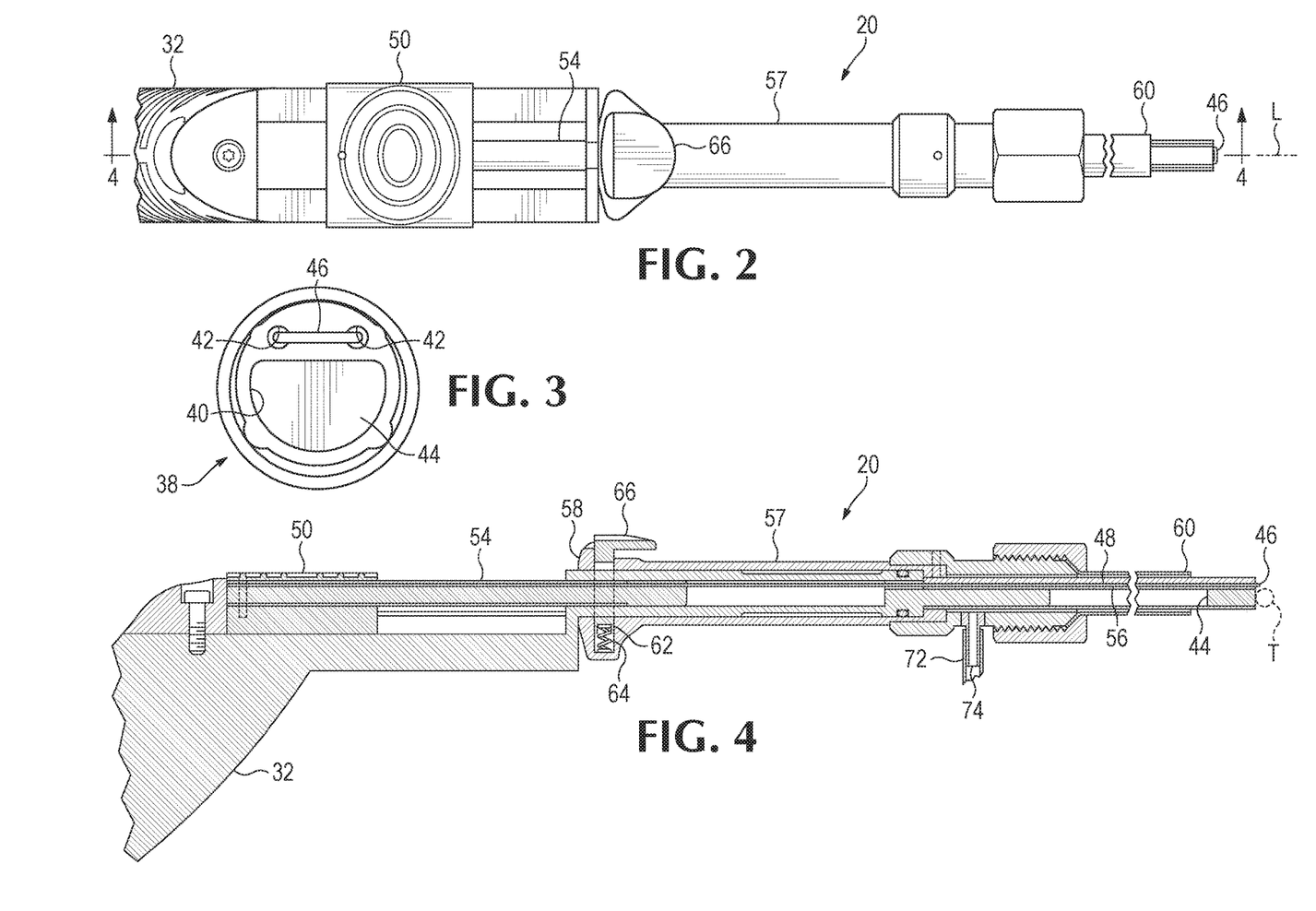
FIG. 2 is a top view of the rail tension extraction device of FIG. 1.
FIG. 3 is a partial front view of the rail tension extraction device of FIG. 1, showing a magnet and a tensioned wire.
FIG. 4 is a sectional view of the rail tension extraction device of FIG. 1 taken along lines 4-4 in FIG. 2, showing the tensioned wire in a retracted position and an outer tube in an unlocking position.

Elongate base 34 includes one or more channels for portions of the engagement assembly and/or securing assembly. In the example shown in FIGS. 1-6, the elongate base 34 includes a cavity 40 and two spaced channels 42 separate from the cavity. As shown in FIG. 3, cavity 40 occupies more than half of the total diameter (or length and/or width) of the elongate base and is larger than the two spaced channels. In some examples, the elongate base may be substantially hollow except for the two spaced channels, such as a double-lumen tube. In other examples, the elongate base is solid other than the cavity and two spaced channels. The elongate base may sometimes be referred to as a "core catheter."

Handle 32 of the base assembly may be any suitable handle. In the example shown in FIGS. 1-6, the handle is in the form of a pistol grip (also may be referred to as a "handle grip"). The base assembly may include other handles, such as a T-grip (or crutch), a D-grip (or YD grip), etc., or may include a knob or other structure.

Engagement assembly 34 includes any suitable structure attached to or contained within cavity 40 of second end portion 38 and configured to engage one or more targets in the patient's body, such as wire guides, cardiac leads, etc. In the example shown in FIGS. 1-6, the engagement assembly includes at least one magnetic attraction element 44, such as at least one magnet, received in second end portion 38 and configured to engage a metallic target. Any suitable magnets may be used, such as neodymium iron boron (NdFeB) and samarium cobalt (SmCo). When neodymium iron boron (or neodymium) magnets are used, suitable grades include N50 and N52.

The magnetic attraction element can be any suitable shape(s) and/or size(s). In the example shown in FIGS. 1-6, the magnetic attraction element is shaped and sized to fit within cavity 40 of second end portion 38. However, other examples of the rail tension extraction device may include magnetic attraction element(s) that have larger or smaller dimensions than cavity(ies) of the elongate base, and/or that have a shape different from the elongate base. When the magnetic attraction element(s) have dimensions larger than cavity(ies) and/or channel(s) of the elongate base (and thus cannot fit within the cavity(ies) and/or channel(s)), the magnetic attraction element(s) may be attached to the second end portion instead of being contained within the cavity and/or channel. When attached to the second end portion, the dimensions of the magnetic attraction element(s) still allow the element(s) to be at least partially contained within a portion of the locking assembly to allow the locking assembly to lock the target, as further discussed below. The engagement assembly and/or the magnetic attraction element may sometimes be referred to as a "stylet."

Securing assembly 26 may include any suitable structure configured to secure the target to engagement assembly 24, such as once the target is engaged by the engagement assembly. In the example shown in FIGS. 1-6, the securing assembly includes at least one capture element 46, at least one follower element 48, and at least one control element 50. The capture element may include any suitable structure configured to be slidably received in channels 42 of second end portion 38 and to capture and/or secure the target to the elongate base, such as by at least partially surrounding or surrounding the target. The capture element is configured to move and/or slide relative to the base assembly between a retracted position in which the capture element (or an end or working portion of the capture element) is within the channels of the elongate base, and an extended position in which the capture element (or the end or working portion of the capture element) is outside those channels.

Figure 8:
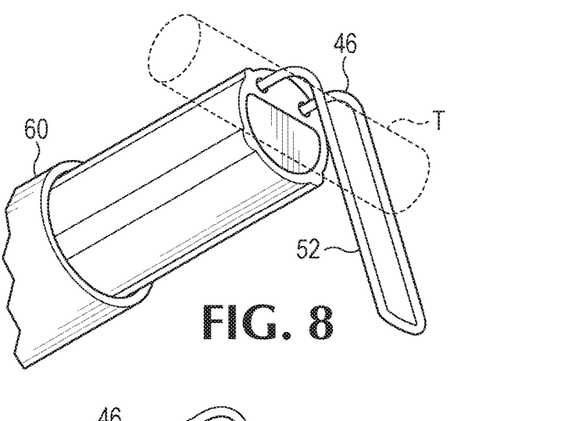
Figure 9:
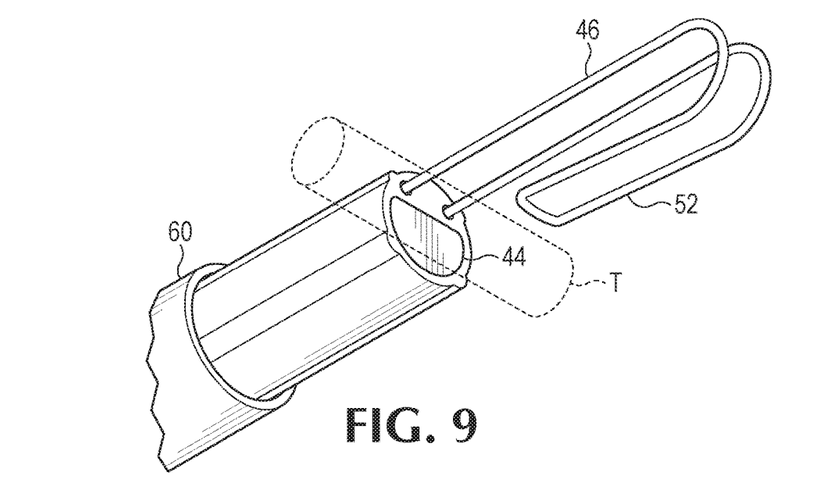
Figure 10:
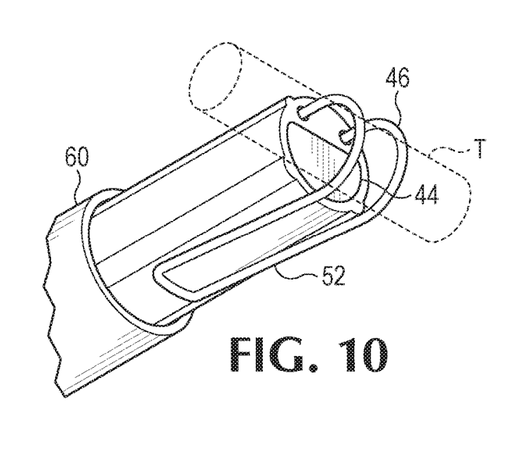

In the example shown in FIGS. 1-6, capture element 46 is a wire (such as Nitinol wire or memory wire) having first and second ends. The first end is attached to follower element 48 and the second end includes a hook and/or loop 52 (as shown in FIG. 9). The wire is tensioned such that the second end extends initially along a longitudinal axis L of the elongate base when the second end is just outside the channel. As the second end moves further way from the opening of the cavity, the second end pivots along an axis that is perpendicular (or substantially perpendicular) to the longitudinal axis of the elongate base so that the second end wraps or encircles around a target T engaged by the engagement assembly, as shown in FIGS. 8-10. Although FIGS. 1-6 show capture element as a hook, the capture element may alternatively, or additionally, include other structural components, such as a pole or tube having a second end with two or more gripping fingers, a basket, and/or other capturing structure(s).

Follower element(s) 48 may include any suitable structure configured to connect the control and capture elements to allow the control element to move the capture element(s) between the extended and retracted positions. In the example shown in FIGS. 1-6, the follower elements include a follower pole or follower tube 54 attached to the control element and a guide wire 56 attached to the follower tube at one end and the capture element on the other end (i.e., disposed between the follower tube and the capture element) such that movement of the control element translates into movement of the capture element. In other words, movement of the control element translates into movement of the capture element between the retracted and extended positions.

Control element 50 may include any suitable structure manipulable by a user to move the capture element between the retracted and extended positions. In the example shown in FIGS. 1-6, control element includes at least one button that is movably or slidably connected to the base assembly such that the button is configured to move or slide between first and second positions. The button may sometimes be referred to as a "control slide." The button may be positioned at any suitable portion of the device. In the example shown in FIGS. 1-6, the button is proximate or adjacent the handle to allow a user to grab the handle with his or her hand and operate the button with the same hand. Although control element is shown to include a button, the control element may alternatively, or additionally, include other control structures, such as a control knob or a lever that is pivotably or rotatably mounted to the base assembly, a push or pull handle slidably mounted to the base assembly, etc.

Locking assembly 28 may include any suitable structure configured to lock a target to base assembly 22, such as between capture element 46 and locking assembly 28. In the example shown in FIGS. 1-6, the locking assembly includes at least one outer sheath or tube 57 having a proximal end 58 and a distal end 60. The outer tube flares outward or has a proximal end with a larger diameter than the distal end (e.g., knob-shaped) to facilitate manipulation by a user. The outer tube is hollow or at least partially hollow and slides over or receives the elongate base of the base assembly such that the outer tube moves or slides between locking and unlocking positions. In some examples, the outer tube (or the distal end of the outer tube) has an inner diameter that is no more than about 1.5 or 2 times larger than the outer diameter of the elongate base (or second end portion of the elongate base). In other examples, the outer tube (or the distal end of the outer tube) has an inner diameter that is the sum of the outer diameter of the elongate base (or second end portion of the elongate base) and about twice the thickness of the wire. The locking assembly further includes a friction pad 62, at least one spring 64, and a release button 66. The friction pad contacts the elongate base and secures the outer tube in its position via urging of spring(s) 64 toward the elongate base. Release button 66 allows a user to move the friction pad away from the outer tube (e.g., by pushing downward on the release button) to allow movement of the outer tube between the locking and unlocking positions.

Figure 5:
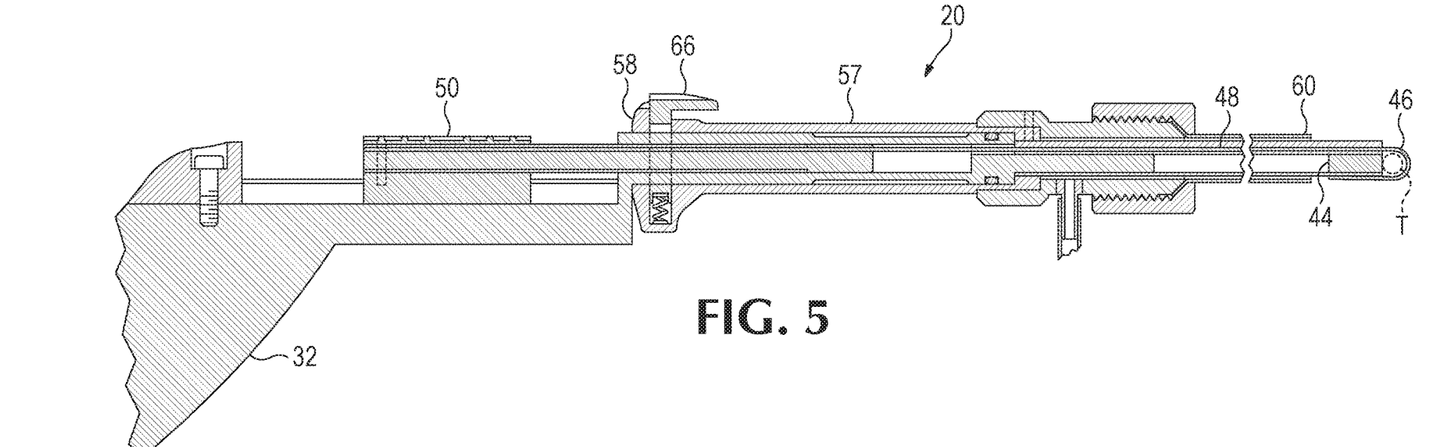
FIG. 5 is the sectional view of FIG. 4, showing the tensioned wire in an extended position and the outer tube in the unlocking position.
Figure 6:
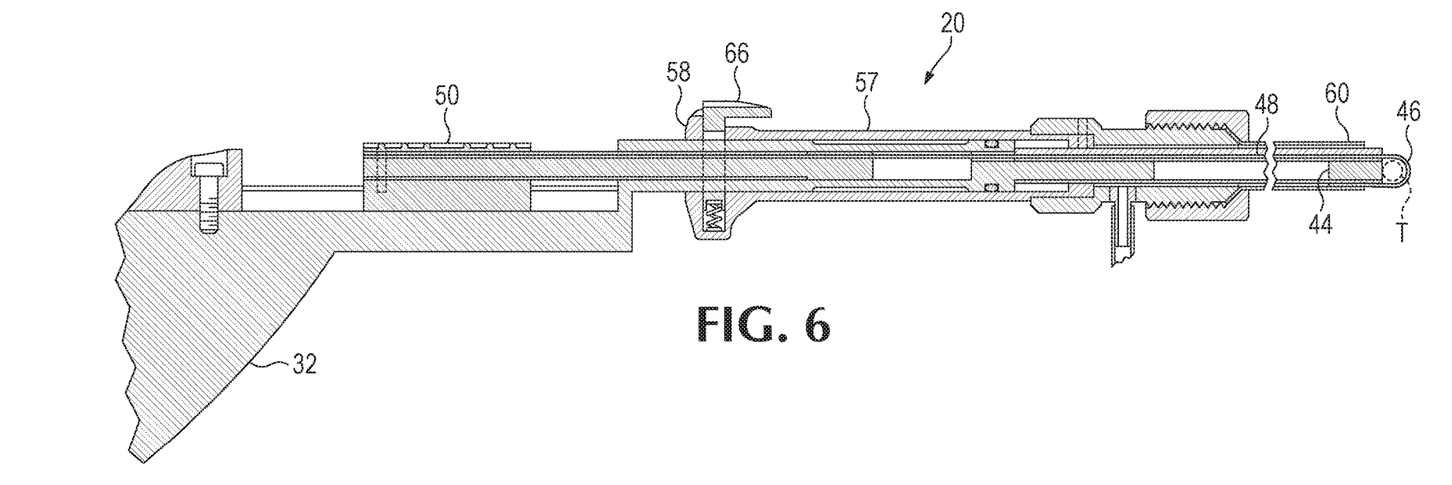
FIG. 6 is the sectional view of FIG. 4, showing the tensioned wire in the extended position and the outer tube in the locking position to secure the metallic target to the rail tension extraction device.
Figure 7:
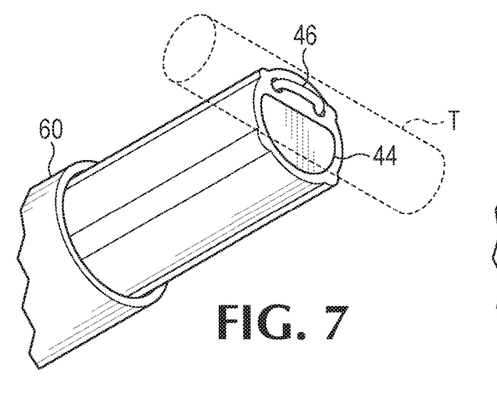
FIGS. 7-11 are partial perspective views of the tensioned wire moving from the retracted position to the extended position, and of the outer tube moving from the unlocking position to the locking position, to secure a metallic target to the rail tension extraction device.
Figure 11:
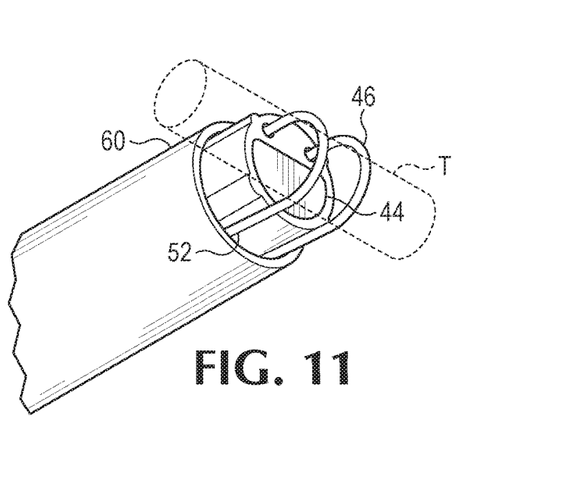

In the locking position, distal end 60 is adjacent magnet 44 and capture element 46 to secure the target therebetween. Specifically, distal end 60 receives an end portion of hook 52 of capture element 46 to lock or secure the target between magnet 44 and capture element 46, as shown in FIGS. 6 and 11. In other words, the end portion of the hook is disposed between (or sandwiched by) the distal end and the second end portion when the outer tube is in the locking position. In some examples, the target is disposed between and in direct contact with both the distal end and the capture element. In the unlocking position, distal end 60 is spaced magnet 44 and capture element 46 such that the target is not locked or secured between the magnet and the capture element, as shown in FIGS. 5 and 10. Although locking assembly is shown to include at least at least one outer sheath or tube, the locking assembly may include hollow structures of other shapes that are complementary or corresponding to the shape of the base assembly, particularly when the base assembly does not include a cylindrically-shaped elongate tube. The outer sheath or tube may sometimes be referred to as a "lock catheter."

Fluid assembly 30 may include any suitable structure configured to fluidly connect a source of fluid with the inner space between the outer tube and the elongate base. In the example shown in FIGS. 1-6, the fluid assembly includes a source coupler 68, a valve 70, tubing 72, and an outer tube coupler 74. The source coupler allows a user to couple the fluid assembly to a fluid source, such as a source of saline solution. The valve controls flow of the fluid to the inner space between the other tube and the elongate tube and is configured to move between open and closed positions. The tubing fluidly connects the valve and the outer tube coupler to deliver the fluid from the valve to the above inner space.

Figures 12, 13:
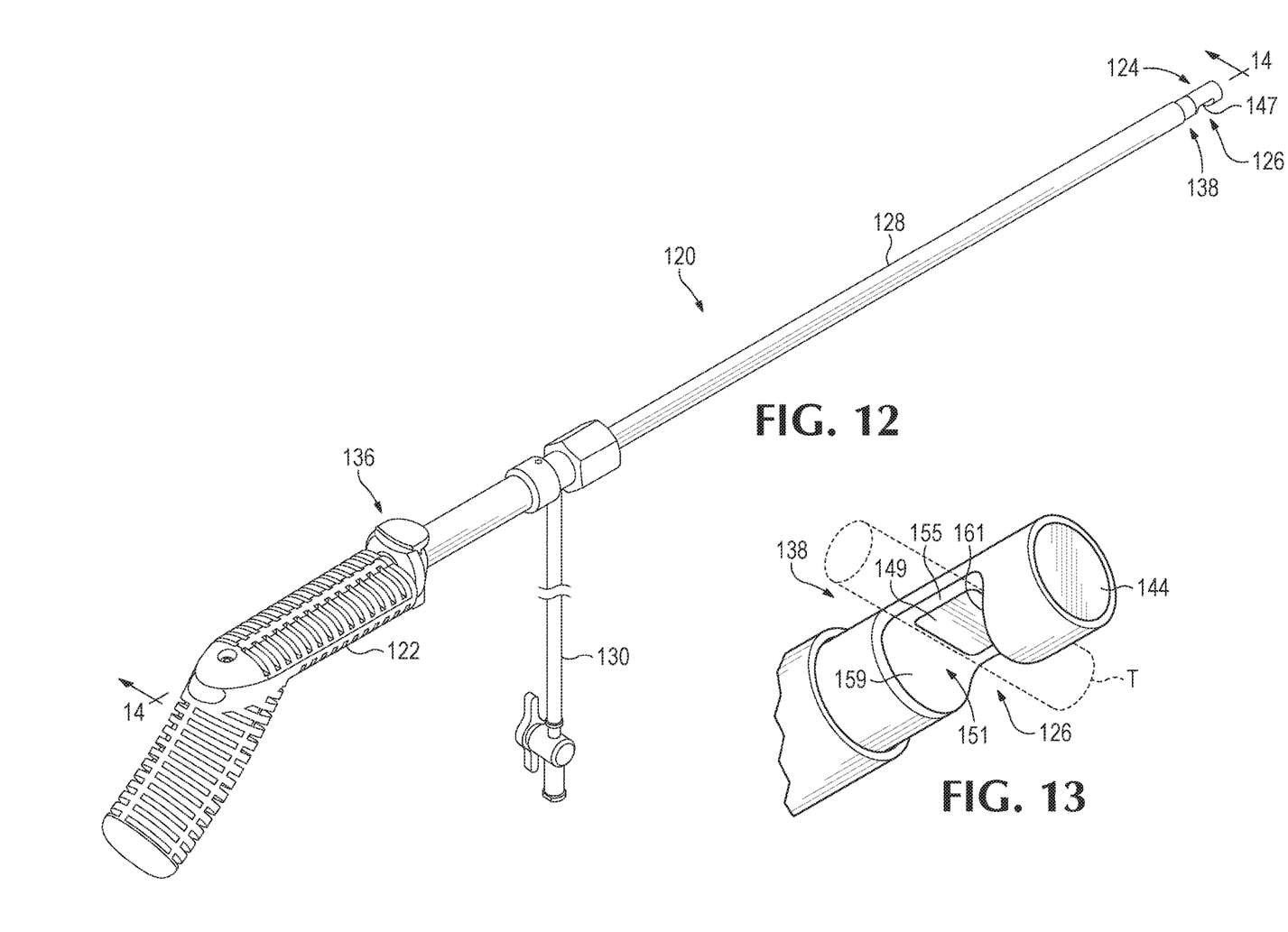
FIG. 12 is a perspective view of another example of a rail tension extraction device of the present disclosure.
FIG. 13 is a partial view of the rail tension extraction device of FIG. 12 showing a C-shaped section and magnets to secure a metallic target.
Figure 14:
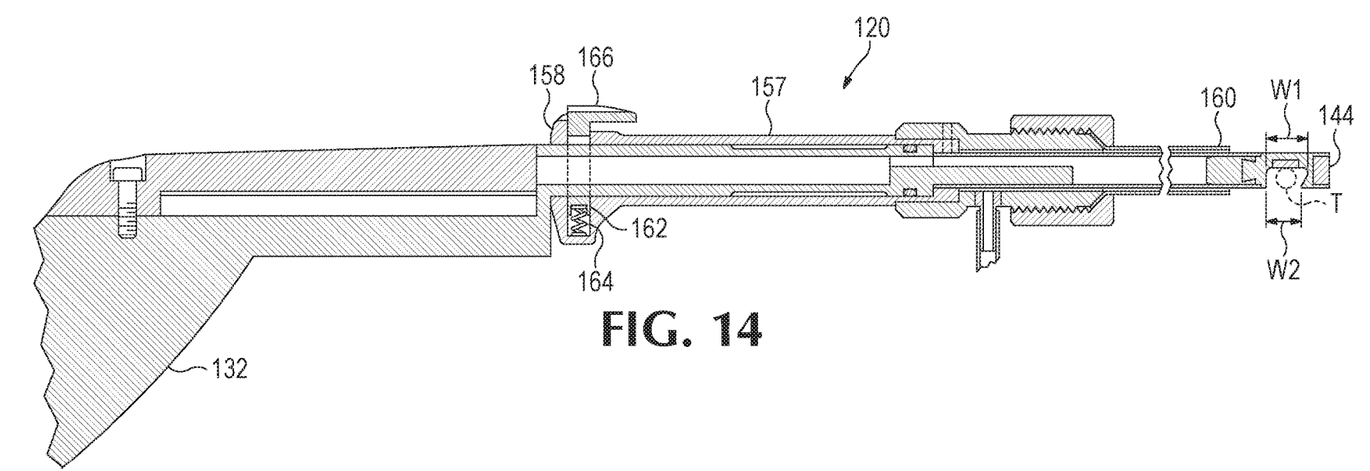
FIG. 14 is a sectional view of the rail tension extraction device of FIG. 12 taken along lines 14-14 in FIG. 12, showing a metallic target engaged by a magnet in a C-shaped section of an elongate base and an outer tube in an unlocking position.

Referring to FIGS. 12-14, another example of a rail tension extraction device of the present disclosure is generally indicated at 120. Unless explicitly excluded, rail tension extraction device 120 may additionally, or alternatively, include one or more components of the other rail tension extraction devices of the present disclosure. Some of the components of rail tension extraction device 120 are labelled 1XX that may be the same or similar to the components labelled XX of rail tension extraction device 20 and thus may be described in lesser detail or no detail at all. For example, base assembly 122 of rail tension extraction device 120 may be similar to base assembly 22 of rail tension extraction device 20.

Figure 15:
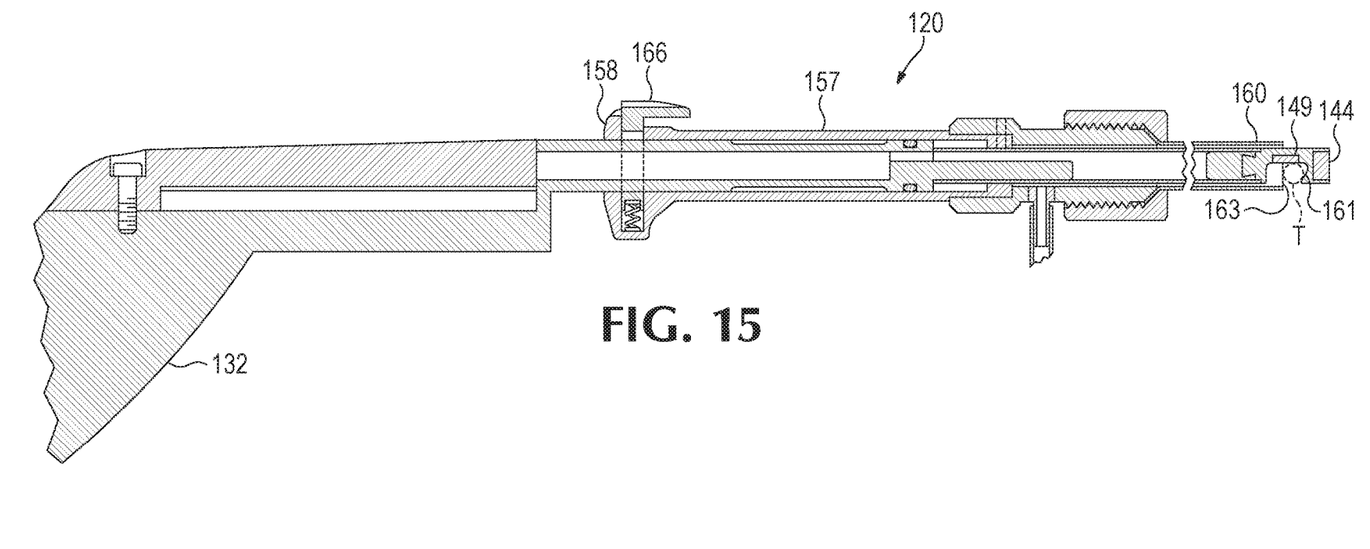
FIG. 15 is the sectional view of FIG. 14 showing the outer tube in a locking position to secure the metallic target to the rail tension extraction device.
Figures 16, 17, 18:
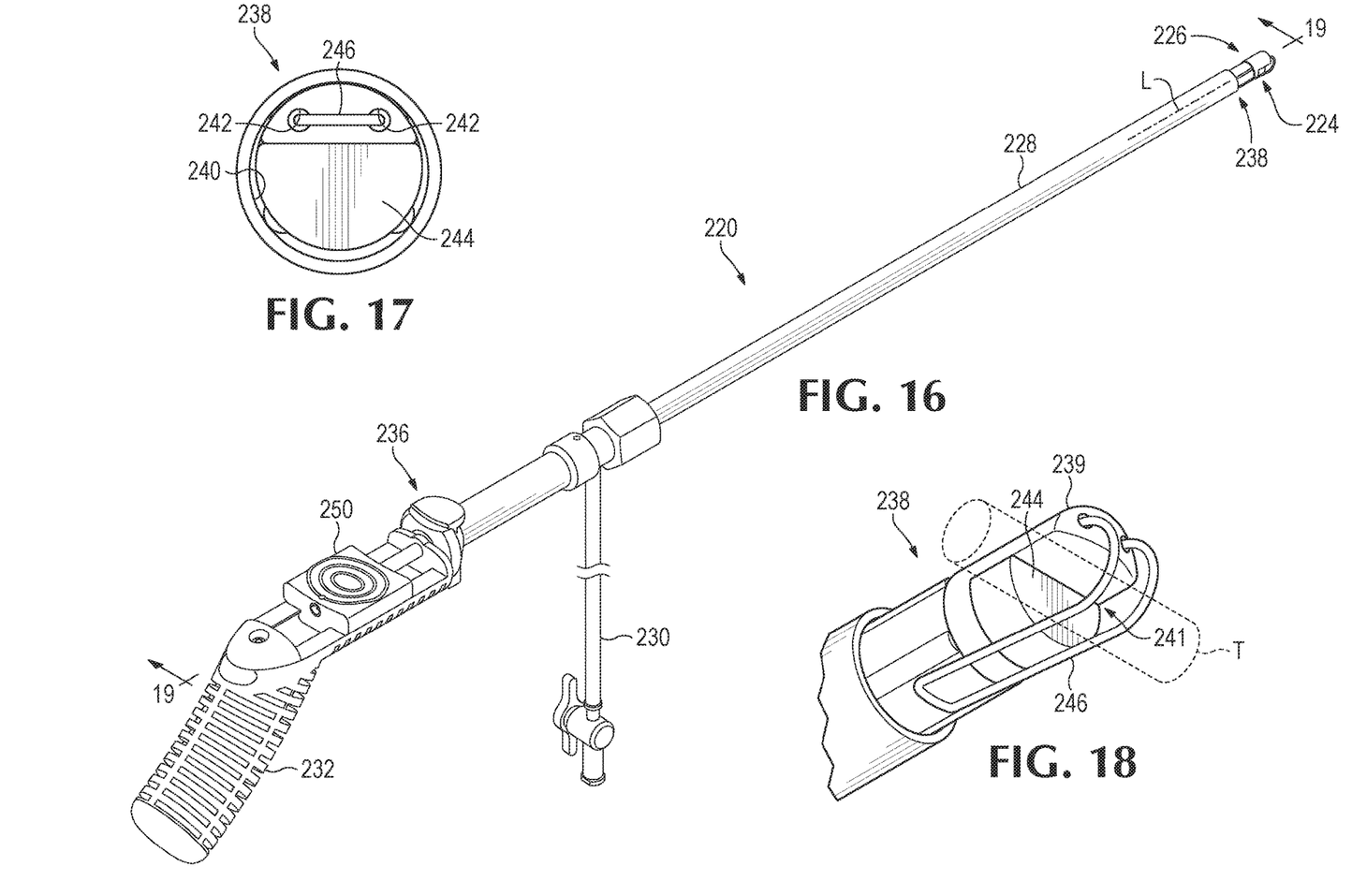
FIG. 16 is a perspective view of a further example of a rail tension extraction device of the present disclosure.
FIG. 17 is a partial front view of the rail tension extraction device of FIG. 16 showing a magnet and a tensioned wire.
FIG. 18 is a partial perspective view of the rail tension extraction device of FIG. 16 showing a tensioned wire and an offset magnet.
Figure 19:
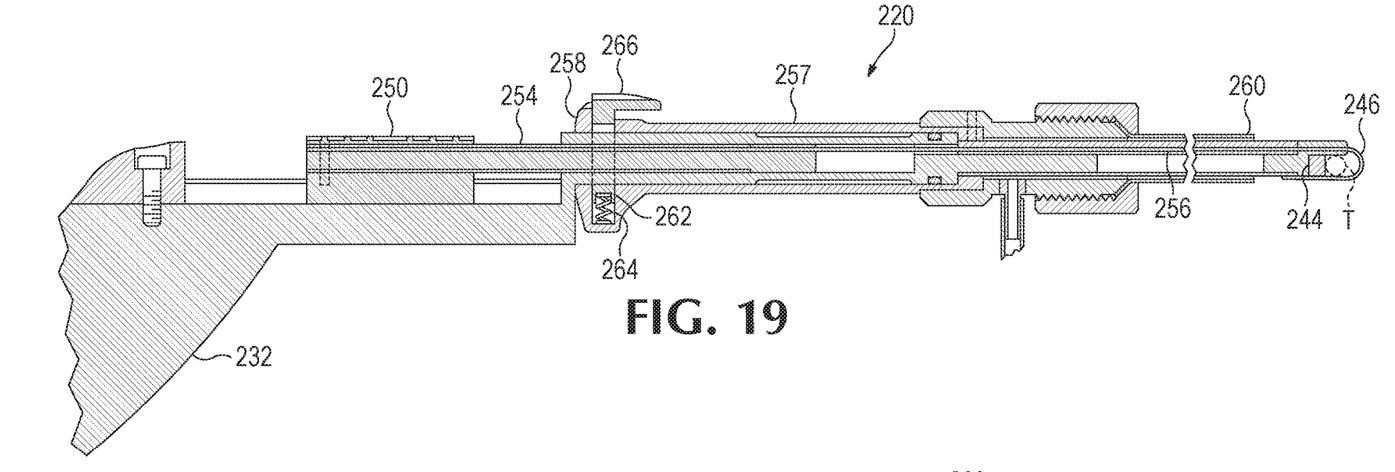
FIG. 19 is a sectional view of the rail tension extraction device of FIG. 16 taken along lines 19-19 in FIG. 16 showing the tensioned wire in an extended position and an outer tube in an unlocking position.
Figure 20:
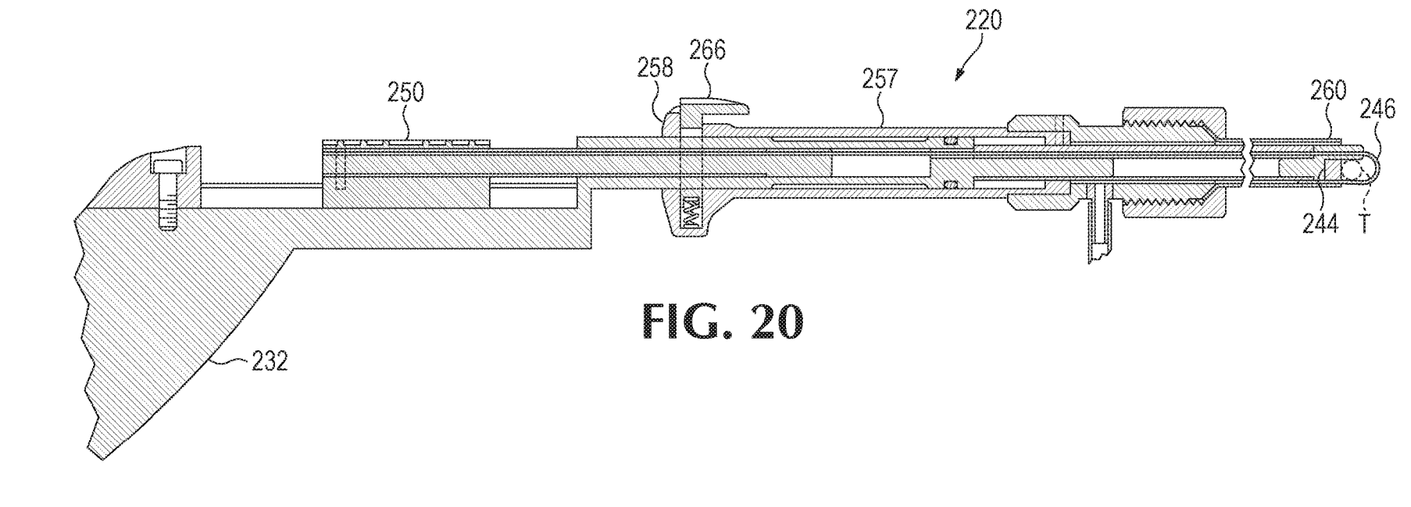
FIG. 20 is the sectional view of FIG. 19 showing the outer tube in a locking position.

Unlike the previous device above, rail tension extraction device 120 does not include a tensioned wire for the capture element and its associated components to move the tensioned wire between extended and retracted position, such as the control element, the follower element, and the two channels discussed above for rail tension extraction device 20. Instead, securing assembly 126 includes capture elements 146 in the form of a notch 147 in second portion 138 and at least a second magnet 149 received in the second end portion adjacent to the notch, as shown in FIGS. 13-15.

Notch 147 may be any suitable shape configured to provide a capture area 151 having a first width W1 with an opening 153 to the capture area having a second width W2 that is smaller than the first width. In the example shown in FIGS. 13-15, the notch is generally wedge-shaped, but the notch may have any suitable shape(s). With notch 147, second end portion 138 may sometimes be described as generally C-shaped. Notch 147 also may be described as being defined by a longitudinal surface 155 of the second end portion that is along the longitudinal axis of the elongate base, and opposed transverse surfaces 159 and 161 of the second end portion (which are generally perpendicular or non-parallel to the longitudinal axis). The longitudinal surface and transverse surfaces define the capture area for the target. In the example shown in FIGS. 13-15, second magnet 149 is received below longitudinal surface 155 (or in a middle area of the C-shaped second end portion).

Opening 153 allows a user to guide device such that the target is received in the capture area. Once the target is in the capture area, longitudinal surface 155 and transverse surfaces 159 and 161 partially surround the target. Magnet 144 and/or second magnet 149 engage the target to maintain the target in the capture area. Moving outer tube 157 to the locking position secures the target between an end 163 of the outer tube and transverse surface 161, as shown in FIG. 15. In other words, the end of the outer tube contacts and/or pushes the target against transverse surface 161 so secure the target to the extraction device.

Referring to FIGS. 16-20, another example of a rail tension extraction device of the present disclosure is generally indicated at 220. Unless explicitly excluded, rail tension extraction device 220 may additionally, or alternatively, include one or more components of the other rail tension extraction devices of the present disclosure. Some of the components of rail tension extraction device 220 are labelled 2XX that may be the same or similar to the components labelled XX of rail tension extraction device 20 and/or the components labelled 1XX of rail tension extraction device 120 and thus may be described in lesser detail or no detail at all. For example, base assembly 222 of rail tension extraction device 220 may be similar to base assembly 22 of rail tension extraction device 20 and base assembly 122 of rail tension extraction device 120.

Rail tension extraction device 220 is similar to rail tension extraction device 20, except that extraction device 220 includes a different shaped second end portion 238. A portion 239 of the second end portion having two spaced channels 242 extends beyond magnet 244 along longitudinal axis L. In other words, unlike rail tension extraction device 20, a top surface of magnet 244 is not co-planar with the openings of channels 242 because magnet 244 is offset relative to the channels and capture element 246. When capture element 246 is in the extended position shown in FIG. 18, capture element 246, magnet 244, and portion 239 define a capture area 241 for the target.

Figure 21:
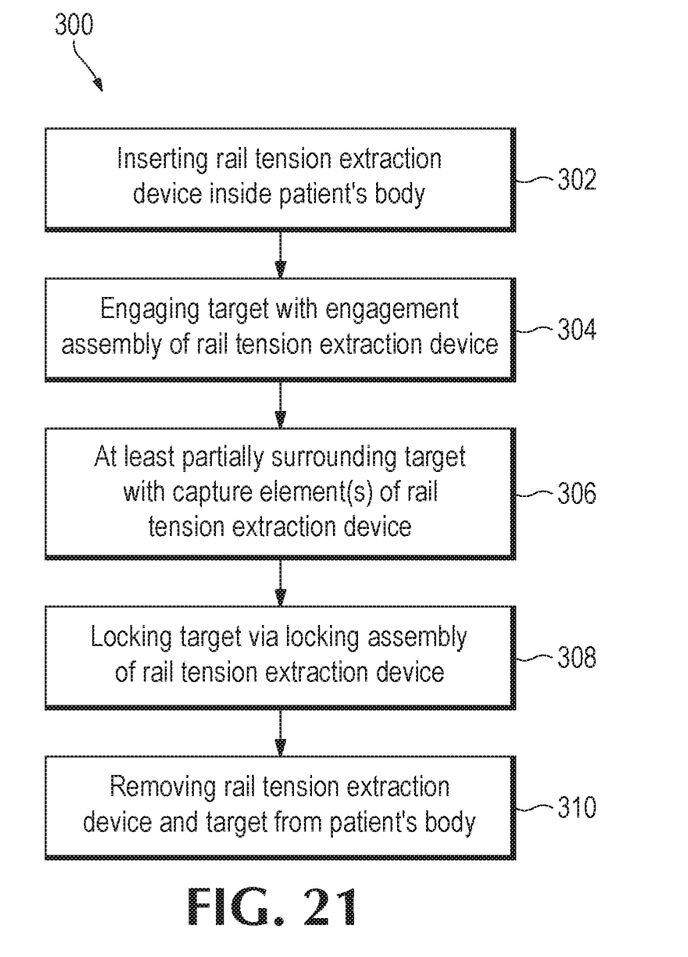
FIG. 21 is a flowchart showing an example of a method of extracting a metallic target from inside a patient's body.

FIG. 21 is a flowchart showing an example of a method of extracting a metallic target in a patient's body, generally indicated at 300. Although particular steps are shown in the example of FIG. 21, other examples of the method may add, omit, modify, or substitute one or more steps. Additionally, other examples of the method may have a different order or sequence of steps instead of the particular sequence of steps shown in FIG. 21.

The first step of the method includes inserting a rail tension extraction device (e.g., extraction device 20, 120, or 220) inside a patient's body at 302, such as adjacent to a desired metallic target via any suitable access point (e.g., inferior vena cava). A guiding sheath may be inserted prior to inserting the extraction device into the guiding sheath.

The second step of the method includes engaging the metallic target with an engagement assembly (e.g., at least one magnet) of the rail tension extraction device at 304. The rail tension extraction device is moved or advanced into the patient adjacent or proximal the target(s) until the engagement assembly engages the target.

Once the target is engaged, the target may be at least partially surrounded (or fully surrounded) by a capture element of the rail tension extraction device at 306. When the capture element is a tensioned wire or wire loop, the wire is moved to the extended position to wrap around the target. When the capture element is a notch and a second magnet, steps 304 and 306 may include navigating the extraction device such that the target is received in the notch and engaged by the magnet(s).

The target may then be locked via the locking assembly of the rail tension extraction device, such as by moving the outer tube of the extraction device to the locking position to secure or lock the target at 308. When the capture element is a wire, the distal end of the outer tube contacts and secures an end portion of the wire in the locking position. When the capture element includes a notch, the distal end of the outer tube contacts the target and presses the target against a transverse surface defined by the notch.

Once the target is locked, a rail is created allowing the target to be released and then resecured as necessary until the target is ready to be removed through the desired access point at 310. For example, the target can be removed via the superior vena cava (SVC) after the target is released by the rail tension extraction device, or via the IVC while the target is still secured by the rail tension extraction device. The rail tension extraction device is removed from the guiding sheath, cleaned (such as wiped or flushed with saline solution through the fluid assembly), and inspected before it is used to extract another target.

This section describes additional aspects and features of rail tension extraction devices, presented without limitation as a series of paragraphs, some or all of which may be alphanumerically designated for clarity and efficiency. Each of these paragraphs can be combined with one or more other paragraphs, and/or with disclosure from elsewhere in this application in any suitable manner. Some of the paragraphs below expressly refer to and further limit other paragraphs, providing, without limitation, examples of some of the suitable combinations.

A0. A rail tension extraction device, comprising a base assembly having a handle and an elongate tube, the elongate tube includes first and second ends and having a channel along the length of the tube between the first and second ends, the handle is attached to the first end; an engagement assembly attached to the second end and configured to engage a metallic target; at least one capture element received within the channel and configured to move between an extended position in which at least a portion of the capture element extends outside the channel, and a retracted position in which the at least a portion of the capture element is within the channel; and an outer tube that slidably receives the elongate tube and includes opposed proximal and distal ends, the outer tube is configured to move relative to the elongate tube between a locking position in which the distal end of the outer tube is adjacent to the at least a portion of the capture element to secure the metallic target therebetween, and an unlocking position in which the distal end of the outer tube is spaced from the at least a portion of the capture element.

A1. The device of paragraph A, wherein the engagement assembly is a magnet.

A2. The device of paragraph A1, wherein the magnet is a neodymium magnet.

A3. The device of paragraph A2, wherein the magnet is a N52 neodymium magnet.

A4. The device of any of paragraphs A0-A3, wherein the at least one capture element is a wire having an end with a hook.

A5. The device of paragraph A4, wherein the wire is tensioned such that the hook wraps around the metallic target when the hook is extended outside the channel and the target is engaged by the engagement assembly.

A6. The device of paragraph A5, where the channel defines an elongate axis, and wherein the wire is tensioned such that the hook pivots about an axis that is substantially perpendicular to the elongate axis.

A7. The device of any of paragraphs A4-A6, further comprising a control element movably attached to the base assembly and configured to move the capture element between the extended and retracted positions.

A8. The device of paragraph A7, wherein the control element is a button that is slidably attached to the base assembly.

A9. The device of any of paragraphs A7-A8, wherein the control element is positioned to allow a user to manipulate the control element with a thumb of the user's hand while grasping the handle with the same hand.

B0. A method of extracting a metallic target from inside a patient via the rail tension extraction device of any of paragraphs A0-A9.

B1. The method of B0, wherein the metallic target is a lead.

B2. The method of B1, wherein the lead is from a pacemaker device.

C0. A method of extracting a metallic target from inside a patient via a rail tension extraction device, comprising inserting the rail tension extraction device into an access point of the patient, moving the device to allow at least one magnet of the device to engage the metallic target, wrapping a wire loop of the device around the metallic target, and moving an outer sheath of the device to lock the metallic target between the wire loop and the outer sheath.

C1. The method of paragraph C0, where the wire loop is tensioned to wrap around the metallic target, wherein wrapping a wire loop of the device around the metallic target includes extending the wire loop outside a channel of the device when the metallic target is engaged by the at least one magnet.

C2. The method of any of paragraphs C0-C1, further comprising inserting a guiding sheath into the access point of the patient, wherein inserting the rail tension extraction device includes inserting the rail tension extraction device through the guiding sheath.

Additional background information and other examples of rail tension extraction devices and methods of using rail tension extraction devices are provided below In the current state of medical practice dealing with implantable leads, Pacemaker, ICD (Implantable Cardiac Defibrillator) and Neuro stimulation leads, it is well known of the indications of having to remove said leads for various reasons. Those reasons may consist of electrical failure, mechanical failure, recalled from manufacturer, infection, occlusion and about 25 more indications which are forecasted to increase every couple of years.

There are few known ways to remove leads from the patient. Using a laser, using mechanical rotational cutting tools, blunt dissection, cardiac surgery and from using femoral rails and applying traction. However, lead removal is presently and very cumbersome and frustrating process. Regarding snaring from the femoral access, the rail can be used as a standalone tool which can be time consuming from the standpoint of the inability to effectively lock onto the targeted lead because of several reasons, including encapsulation, lead breakage, and the difficulties associated with locating the lead in the same plane while looking on x-ray. The current tools can be hard to manipulate within the small space of the right atrium, SVC (superior vena cava) and the IVC (inferior vena cava). Sometimes this process can take hours. It is well documented about the associated costs of prolonged procedures in the or let alone the patient safety of being under general anaesthesia longer than needed.

Extractions of said leads have a low rate of complication and mortality but there is still some risk associated with the procedure. The current trend with laser and mechanical tools from above through the device pocket via the subclavian vein, innominate vein, SVC RA RV has proven effective and safe, but it requires tension or rail needs to be applied on the lead to pull it away from the lateral wall of the SVC. This allows for the tool to track over the lead and effectively remove the adhesions holding the lead in place, so it can be removed from the body. It is believed this reduces the risk of an SVC tear, which would require an urgent open chest procedure to repair.

From the femoral access removal, the femoral vein is accessed with large sheaths and tools are used to be inserted and guided into the IVC, SVC, and cardiac regions to locate and lock onto the lead and then traction is applied pulling the lead away from the vascular wall and cardiac musculature. This process is also effective but can be very time consuming and has the same complication risk and the approach from above.

The rail tension extraction device of the present disclosure is configured to allow quick engagement of the targeted lead(s) to apply appropriate traction for the aiding in removal of the lead from above. This system consists of a guiding sheath, a lock catheter, an inner catheter, and a stylet.

First the targeted leads will be prepped in the current practice of opening the device pocket, removing the lead(s) from the device (pacemaker, ICD, CRT-D, Neuro-stimulator). The suture tie down sleeves will be removed from the lead and the leads dissected away from the fibrous tissue in the pocket. The lead(s) terminal pin will be removed but cutting them off with heavy cutters. The lead lumen will be check for patency with clearing stylets provided by device company. At this point, the stylet will be inserted into the lead lumen and advanced to the tip of the lead or as far as it will advance. When this is placed, we can move to inserting the rail tension extraction device.

The operation will consist of obtaining access in the femoral vein and inserting an introducer sheath. The guiding sheath will be inserted into the sheath over, for example, a 0.035 guide wire to the level of the IVC. The 0.035 guide wire will be removed, the guide sheath flushed with heparinized saline. The lock and core catheters will be inserted into the guiding sheath and advanced to the tip of the guiding sheath. At this point the guiding sheath can be directed by rotational and advance/retraction to better locate the targeted lead(s). Once in the proper position the core catheter is then advanced, the attraction of the stylet will attract the lead in contact with the tip of the core catheter. At this point, core catheter nitinol loop will be advanced allowing the nitinol loop to be advanced over the targeted lead(s). Once the core catheter nitinol loop is over the lead, the lock catheter will be advanced over the leading edge of the loop, to secure the target. Counter traction will now be applied to the lead in the act of pulling down on the lead with the system creating a rail.

Now the extraction from above can be commenced using laser or mechanical tools. At this point, once the traction is applied and the lead in lock with the rail tension extraction device, the stylet can be removed. A lead locking device can now be inserted into the targeted lead(s) lumen and locked into place to enhance the rail from above and utilize the increased rail and traction to safely remove the lead. The tool will be advanced to the location of the loop and at this point can either be removed from the femoral access or the superior approach through the lumen of the said extraction tool.

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. A rail tension extraction device, comprising:
a base assembly having a handle and an elongate base, the elongate base includes opposed first and second end portions, the handle is attached to the first end portion;
at least one magnet received in the second end portion and configured to engage a metallic target;
a capture element received in the elongate base and disposed adjacent to the at least one magnet, the capture element is configured to at least partially surround the metallic target engaged by the at least one magnet; and
an outer tube that slidably receives the elongate base and includes opposed proximal and distal ends, the outer tube is configured to move relative to the elongate base between a locking position in which the distal end of the outer tube is adjacent the capture element and the at least one magnet to secure the metallic target therebetween, and an unlocking position in which the distal end of the outer tube is spaced from the capture element and the at least one magnet, wherein the second end portion includes a cavity and two spaced channels separate from the cavity, and wherein the capture element is received within the two channels and configured to move between an extended position in which at least a portion of the capture element extends outside the two channels, and a retracted position in which the at least a portion of the capture element is within the two channels.

2. The device of claim 1, wherein the capture element is a wire having an end with a hook.

3. The device of claim 2, wherein the wire is tensioned such that the hook wraps around the metallic target when the wire is extended outside the two channels and when the target is engaged by the at least one magnet.

4. The device of claim 3, wherein a portion of the hook is sandwiched between the second end portion of the elongate base and the distal end of the outer tube when the outer tube is in the locking position.

5. The device of claim 1, where the elongate base defines a longitudinal axis, wherein the at least one magnet is received in the cavity, and wherein a portion of the elongate base having the two channels extends beyond the at least one magnet along the longitudinal axis such, when the capture element is in the extended position, the capture element, the at least one magnet, and at the portion of the elongate tube having the two channels define a receiving space for the metallic target.

6. The device of claim 5, wherein the capture element is a wire having an end with a hook.

7. The device of claim 6, wherein the wire is tensioned such that the hook wraps around the metallic target when the wire is extended outside the two channels and the target is engaged by the at least one magnet.

8. The device of claim 7, wherein a portion of the hook is sandwiched between the second end portion of the elongate base and the distal end of the outer tube when the outer tube is in the locking position.

9. The device of claim 1, further comprising a control assembly movably attached to the base assembly and configured to move the capture element between the extended and retracted positions.

10. The device of claim 9, wherein the control assembly includes a button that is slidably attached to the base assembly.

11. The device of claim 10, wherein the control assembly is positioned to allow a user to manipulate the control element with a thumb of the user's hand while grasping the handle with the same hand.

12. A rail tension extraction device, comprising:
a base assembly having a handle and an elongate base, the elongate base includes opposed first and second end portions, the handle is attached to the first end portion;
at least one magnet received in the second end portion and configured to engage a metallic target;
a capture element received in the elongate base and disposed adjacent to the at least one magnet, the capture element is configured to at least partially surround the metallic target engaged by the at least one magnet; and
an outer tube that slidably receives the elongate base and includes opposed proximal and distal ends, the outer tube is configured to move relative to the elongate base between a locking position in which the distal end of the outer tube is adjacent the capture element and the at least one magnet to secure the metallic target therebetween, and an unlocking position in which the distal end of the outer tube is spaced from the capture element and the at least one magnet, wherein the second end portion includes a cavity and two spaced channels separate from the cavity and wherein the at least one magnet is received in the cavity of the elongate base.

13. A rail tension extraction device, comprising:
a base assembly having a handle and an elongate base, the elongate base includes opposed first and second end portions, the handle is attached to the first end portion;
at least one magnet received in the second end portion and configured to engage a metallic target;
a capture element received in the elongate base and disposed adjacent to the at least one magnet, the capture element is configured to at least partially surround the metallic target engaged by the at least one magnet; and
an outer tube that slidably receives the elongate base and includes opposed proximal and distal ends, the outer tube is configured to move relative to the elongate base between a locking position in which the distal end of the outer tube is adjacent the capture element and the at least one magnet to secure the metallic target therebetween, and an unlocking position in which the distal end of the outer tube is spaced from the capture element and the at least one magnet, where the elongate base defines a longitudinal axis, wherein the capture element includes a notch in the second end portion and a second magnet, wherein the notch is defined by a longitudinal surface that is parallel to the longitudinal axis and two transverse surfaces that are generally perpendicular to the longitudinal axis, and wherein the second magnet is received below the longitudinal surface such that the second magnet engages the metallic target when the metallic target is in the notch.

14. The device of claim 13, wherein the metallic target is disposed between the distal end of the outer tube and one of the two transverse surfaces when the outer tube is in the locking position.

15. A method of extracting a metallic target that is inside a patient's body, comprising:
inserting a rail tension extraction device inside a patient's body;
engaging the metallic target with at least one magnet of the rail tension extraction device;
at least partially surrounding the metallic target that is engaged by the at least one magnet with a capture element of the rail tension extraction device;
locking the at least partially surrounded metallic target by advancing an outer tube of the rail tension extraction device toward the metallic target; and
removing the rail tension extraction device and the locked metallic target from the person's body, wherein at least partially surrounding the metallic target that is engaged by the at least one magnet includes at least partially surrounding the metallic target with a tensioned wire of the rail tension extraction device.

16. The method of claim 15, wherein at least partially surrounding the metallic target that is engaged by the at least one magnet includes:
positioning the metallic target in a notch of the rail tension extraction device; and
engaging the metallic target with a second magnet adjacent to the notch when the metallic target is positioned in the notch.

17. The method of claim 16, wherein locking the at least partially surrounded metallic target includes contacting the metallic target with an outer tube of the rail tension extraction device and pushing the metallic target against a surface of the notch.

* * * * *